United States Patent [19]

Torii et al.

[11] Patent Number: 4,789,740

[45] Date of Patent: Dec. 6, 1988

[54] HALOGENATION PROCESS FOR PREPARING 2-(OXOAZETIDINYL)-3-CHLOROMETHYL-3-BUTENOATE

[75] Inventors: Sigeru Torii; Hideo Tanaka, both of Okayama; Yuzuru Ogata, Tokushima; Michio Sasaoka, Tokushima; Norio Saito, Tokushima; Shigemitsu Nagao, Tokushima, all of Japan

[73] Assignee: Otsuka Kagaku Yakuhin Kabushiki Kaisha, Osaka, Japan

[21] Appl. No.: 23,970

[22] Filed: Mar. 9, 1987

Related U.S. Application Data

[63] Continuation of Ser. No. 861,626, May 7, 1986, abandoned, which is a continuation of Ser. No. 582,885, Feb. 23, 1984, abandoned.

[30] Foreign Application Priority Data

Mar. 10, 1983 [JP] Japan ................................. 58-40179

[51] Int. Cl.[4] ..................... C07B 39/00; C07D 205/08
[52] U.S. Cl. ..................................... 540/358; 260/694
[58] Field of Search .......................................... 544/358

[56] References Cited

U.S. PATENT DOCUMENTS

| 4,007,202 | 2/1977 | Verweij | 260/239 A |
|---|---|---|---|
| 4,079,181 | 3/1978 | Tsuji | 540/357 |
| 4,220,766 | 9/1980 | Tsuji | 540/361 |
| 4,430,268 | 2/1984 | Cooper | 540/361 |
| 4,443,598 | 4/1984 | Yoshioka | 540/360 |
| 4,482,491 | 11/1984 | Torii | 544/16 |
| 4,532,077 | 7/1985 | Torii | 260/239 A |

FOREIGN PATENT DOCUMENTS 57-59896  4/1982  Japan .

OTHER PUBLICATIONS

Kamya et al, Tet. Letters 1973, 3001-4.
Uneyama, Tet. Letters 1983, 2857.
Uneyama, Chem Letters 1984, 529.
Mastragostino, *Electroanalytical Chem.*, 56, 117 (1974).
Cooper II, Tet. Letters 21, 781 (1980).
Yoshioka I, Tet. Letters 21, 3J 1-354 (1980).
Torii, Tet. Letters 23, 2187 (1982).

*Primary Examiner*—Mark L. Berch
*Attorney, Agent, or Firm*—Larson and Taylor

[57] ABSTRACT

A process for preparing an azetidinone derivative represented by the formula (I)

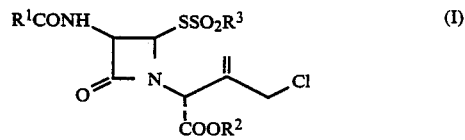

wherein $R^1$ represents an aryl group, arylmethyl group or aryloxymethyl group, $R^2$ represents hydrogen atom or a carboxyl-protecting group and $R^3$ represents an alkyl group or aryl group, the process comprising reacting an azetidinone derivative represented by the formula (II)

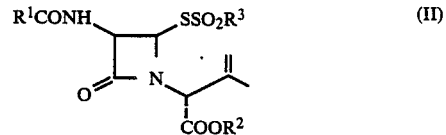

wherein $R^1$, $R^2$ and $R^3$ are as defined above with a chlorinating agent.

12 Claims, No Drawings

HALOGENATION PROCESS FOR PREPARING 2-(OXOAZETIDINYL)-3-CHLOROMETHYL-3-BUTENOATE

This application is a continuation of application Ser. No. 861,626 filed May 7, 1986 (now abandoned), which is a continuation of appliction Ser. No. 582,885 filed Feb. 23, 1984 (now abandoned).

The invention relates to a process for preparing azetidinone derivatives and more particularly to a novel process for preparing azetidinone derivatives represented by the formula (I)

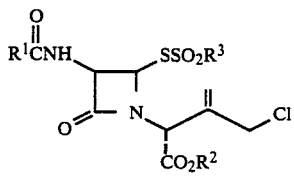

wherein $R^1$ represents an aryl group, arylmethyl group or aryloxymethyl group, $R^2$ represents hydrogen atom or a carboxyl-protecting group and $R^3$ represents an alkyl group or aryl group.

The azetidinone derivatives of the formula (I) are important compounds as intermediates for synthesizing cephalosporin-type antibiotics. For example, the azetidinone derivative of the formula (I) can be converted into 3-chloromethyl cephalosporin according to the process disclosed in Tetrahedron Lett., 23, 2187 (1982).

It is an object of the present invention to provide a commercially favored process for preparing the azetidinone derivatives of the formula (I).

It is another object of the invention to provide a process for preparing the azetidinone derivatives of the formula (I) by carrying out a simple procedure involving reaction under mild conditions.

It is a further object of the invention to provide a process for preparing the azetidinone derivatives of the formula (I) with high purity of nearly 100% in high yield of more than 80%.

Other features of the present invention willbecome apparent from the following description.

According to the present invention, the azetidinone derivatives of the formula (I) can be prepared by reacting an azetidinone derivative of the formula (II)

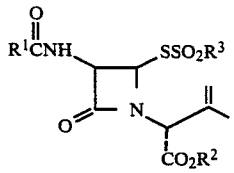

wherein $R^1$, $R^2$ and $R^3$ are as defined above with a chlorinating agent, preferably in a solvent.

Examples of the groups represented by $R^1$ in the formulae (I) and (II) are phenyl, tolyl, xylyl, p-chlorophenyl, p-bromophenyl, p-nitrophenyl, o-nitrophenyl, p-methoxyphenyl and like aryl groups; benzyl, tolylmethyl, xylylmethyl, naphthylmethyl, p-methoxybenzyl, p-nitrobenzyl and like arylmethyl groups; and phenoxymethyl, tolyloxymethyl, xyloxymethyl, p-chlorophenoxymethyl, p-nitrophenoxymethyl, phenylchloromethyl, phenyldichloromethyl and like aryloxymethyl groups.

The carboxyl-protecting groups represented by $R^2$ include those disclosed in Theodora W. Greene, "Protective Groups in Organic Synthesis", Chapter 5. Examples of such groups are methyl, ethyl, propyl, tert-butyl, trichloroethyl, methoxymethyl, methoxyethoxymethyl, isopropoxymethyl, 1-methoxycarbonyl-2-oxopropyl, benzyl, o-nitrobenzyl, p-nitrobenzyl, o,p-dinitrobenzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, phenacyl, p-bromophenacyl, benzyloxymethyl, trityl, α-diphenylethyl, α-p-methoxyphenylethyl, α-p-methoxyphenyl-β-trichloroethyl, cumyl, fluorenyl, etc.

Examples of the alkyl groups represented by $R^3$ are methyl, ethyl, propyl, isopropyl, butyl, tert-butyl, pentyl, hexyl, heptyl, octyl, nonyl, decyl, etc. Examples of the aryl groups of $R^3$ are phenyl, tolyl, xylyl, p-chlorophenyl, p-bromophenyl, p-nitrophenyl, o-nitrophenyl, p-methoxyphenyl, etc.

The azetidinone derivatives of the formula (II) to be used as the starting material in the present invention are known compounds and can be easily prepared by the process disclosed in e.g., Japanese Unexamined Patent Publication No. 129590/1975.

Examples of the solvents useful in the present invention are halogenated lower hydrocarbon, aromatic hydrocarbon, di-lower alkyl-ether, cyclic ether, di-lower alkoxy-ethane, ester of lower carboxylic acid, etc. The solvents are used singly or in mixture. Preferred examples of useful solvents are chloroform, dichloromethane, dichloroethane, carbon tetrachloride, benzene, chlorobenzene, diethyl ether, tetrahydrofuran, dioxane, 1,2-dimethoxyethane, 1,2-diethoxyethane, 1,2-dibutoxyethane, 1,2-dibenzyloxyethane, 1,2-diacetoxyethane, ethyl formate, ethyl acetate, ethoxyethyl acetate, etc.

The chlorinating agent useful in the process of this invention includes a broad range of compounds heretofore known, such as $Cl_2$, $R^4OCl$ wherein $R^4$ represents an alkyl group, HOCl, $Cl_2O$ and the like. The chlorinating agent is used as it is or as dissolved in an inert organic solvent. The inert organic solvent to be used can be any of those exemplified above. $Cl_2$ may be used in the form of chlorine gas or a solution of chlorine gas in an inert organic solvent, preferably carbon tetrachloride, dichloromethane, dichloroethane, chloroform or like halogenated lower hydrocarbon. Examples of $R^4OCl$ are methoxy chloride ($CH_3OCl$), ethoxy chloride ($C_2H_5OCl$), isopropoxy chloride (($CH_3)_2CHOCl$), tert-butoxy chloride (($CH_3)_3COCl$) and like alkoxy chlorides. $R^4OCl$ is employed preferably as dissolved in an inert organic solvent, particularly carbon tetrachloride, dichloromethane, dichloroethane, chloroform or like halogenated lower hydrocarbon. HOCl is employed preferably as dissolved in an inert organic solvent, particularly di-lower alkyl-ether. $Cl_2O$ is used as it is or preferably as dissolved in an inert organic solvent, particularly carbon tetrachloride. The amount of the chlorinating agent is not particularly limited but can be suitably determined over a wide range. Usually about 1 to about 7 equivalents, preferably about 1 to about 3 equivalents, of the agent is employed relative to the compound (II).

The reaction of the present invention can be conducted in the presence of a compound capable of trapping hydrogen chloride. Examples of such trapping agents are propylene oxide, butylene oxide and the like epoxides; hydroxide, carbonate and dicarbonate of alkali metal such as potassium, sodium or lithium; molecular sieve; polyvinyl pyridine; etc. The amount of the trapping agent is generally about 1 to about 100 equivalents, favorably about 1 to about 30 equivalents relative to the compound (II).

The reaction of the present invention is also feasible in a mixture of water and a hydrophobic organic solvent. Useful hydrophobic organic solvents are, for example, halogenated lower hydrocarbon, aromatic hydrocarbon, ester of lower carboxylic acid or the like among which chloroform, dichloromethane, dichloroethane, carbon tetrachloride, benzene, chlorobenzene and ethyl acetate are usually used.

The compound (II) as used in the reaction of this invention ranges in concentration from usually about 0.1 to about 50 wt.%, preferably about 1 to about 30 wt.%, based on the organic solvent. The reaction of the present invention is effected at a temperature usually about $-70°$ to about $70°$ C., preferably $-10°$ to about $40°$ C.

After the completion of the reaction, the reaction mixture is extracted, washed with water or treated in other usual manner, followed by distillation of the solvent, whereby the compound (I) is produced. The compound (I) thus obtained is substantially pure and can be used as it is in the subsequent reaction such as cyclization to cephalosporin. When purification is performed, the compound is subjected to recrystallization or column chromatography.

The present invention will be described in detail with reference to the following examples in which Ph stands for phenyl group.

EXAMPLE 1

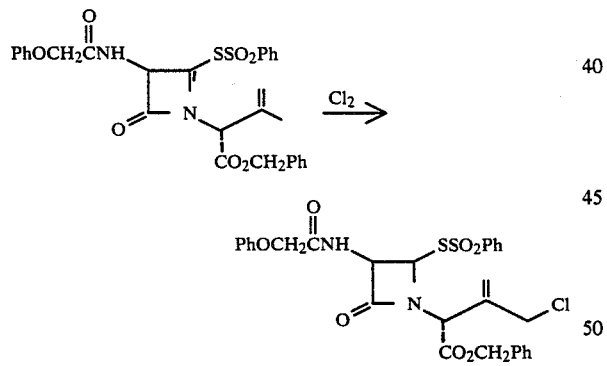

A 2.0 g quantity of benzyl 2-(3-phenoxyacetamido-4-benzenesulfonylthio-2-azetidinone-1-yl)-3-methyl-3-butenate was dissolved in 10 ml of dichloromethane and to the solution was added 5 to ml of water. The mixture was cooled in an ice bath with stirring while thereto was added dropwise over 30 minutes about 10 ml of methylene chloride having dissolved therein 6.9 mmol of chlorine gas. After the addition, the organic layer was separated and the aqueous layer was extracted with dichloromethane. The organic layer thus separated and the dichloromethane layer were washed successively with aqueous solutions each of NaHCO₃, Na₂S₂O₃ and NaCl and dried over anhydrous magnesium sulfate. The solvent was distilled off at reduced pressure. The resulting residue was separated and purified by silica gel column chromatography, giving 1.87 g of benzyl 2-(3-phenoxyacetamido-4-benzenesulfonylthio-2-azetidinone-1-yl)-3-chloromethyl-3-butenate in 88% yield.

EXAMPLE 2

The same procedure as in Example 1 was repeated using the solvents given below in Table 1, producing benzyl 2-(3-phenoxyacetamido-4-benzenesulfonylthio-2-azetidinone-1-yl)-3-chloromethyl-3-butenate in the yields as shown below in Table 1.

TABLE 1

| Solvent | Yield (%) |
| --- | --- |
| Chloroform | 89 |
| Dichloroethane | 95 |
| Benzene | 90 |
| Chlorobenzene | 83 |
| Ethyl acetate | 80 |

EXAMPLE 3

The procedure of Example 1 was followed to give the compounds as indicated below in Table 2 in the yields as shown therein.

TABLE 2

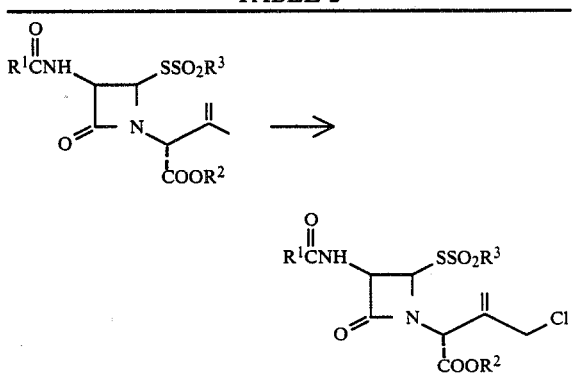

| $R^1$ | $R^2$ | $R^3$ | Yield (%) |
| --- | --- | --- | --- |
| PhCH₂ | CH₃ | Ph | 82 |
| PhCH₂ | CH₃ | p-CH₃—Ph | 90 |
| PhCH₂ | CH₃ | p-Cl—Ph | 85 |
| PhCH₂ | CH₃ | p-NO₂—Ph | 83 |
| PhCH₂ | CH₃ | o-NO₂—Ph | 80 |
| PhCH₂ | PhCH₂ | Ph | 89 |
| PhCH₂ | PhCH₂ | p-CH₃O—Ph | 80 |
| PhCH₂ | PhCH₂ | p-NO₂—Ph | 96 |
| PhCH₂ | p-NO₂—PhCH₂ | p-NO₂—Ph | 91 |
| PhOCH₂ | PhCH₂ | p-NO₂—Ph | 88 |

EXAPLE 4

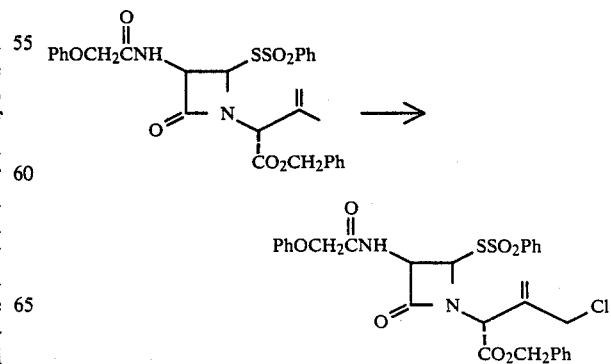

1.0 g quantity of benzyl 2-(3-phenoxyacetamido-4-benzenesulfonylthio-2-azetidinone-1-yl)-3-methyl-3-butenate was dissolved in 10 ml of a benzenedioxane (1:2) mixture. To the solution was added 3 g of NaHCO₃ and the mixture was stirred at room temperature. Thereto was added dropwise over 3 minutes 1.5 ml of carbon tetrachloride having dissolved therein 2.1 mmol of chlorine and the mixture was stirred for 2 hours. The reaction mixture was extracted with ethyl acetate and the extract was subjected to the same subsequent procedure as in Example 1, affording 1.04 g of benzyl 2-(3-phenoxyacetamido-4-benzenesulfonylthio-2-azetidinone-1-yl)-3-chloromethyl-3-butenate in 98% yield.

EXAMPLE 5

The procedure of Example 4 was repeated using the solvents as shown below in Table 3, producing benzyl 2-(3-phenoxyacetamido-4-benzenesulfonylthio-2-azetidinone-1-yl)-3-chloromethyl-3-butenate in the yields as indicated below in Table 3.

TABLE 3

| Solvent | Yield (%) |
| --- | --- |
| Benzene | 89 |
| Chlorobenzene | 85 |
| Dioxane | 92 |
| Tetrahydrofuran | 90 |
| Dimethoxyethane | 88 |
| Diethoxyethane | 85 |
| Benzene-diethoxyethane (2:1) | 92 |
| Benzene-tetrahydrofuran (2:1) | 95 |
| Chlorobenzene-ethyl acetate (1:1) | 87 |

EXAMPLE 6

The compounds as shown below in Table 4 were prepared in the same manner as in Example 4 in the yields as indicated therein.

TABLE 4

$$\underset{\substack{\text{O}\\\|}}{\text{R}^1\text{CNH}}\diagdown\diagup\text{SSO}_2\text{R}^3$$
(azetidinone ring with N–CH(COOR²)–C(=CH₂)–CH₃) → 
$$\underset{\substack{\text{O}\\\|}}{\text{R}^1\text{CNH}}\diagdown\diagup\text{SSO}_2\text{R}^3$$
(azetidinone ring with N–CH(COOR²)–C(=CH₂)–CH₂Cl)

| R¹ | R² | R³ | Yield (%) |
| --- | --- | --- | --- |
| PhCH₂ | PhCH₂ | Ph | 91 |
| PhCH₂ | PhCH₂ | p-NO₂—Ph | 87 |
| PhCH₂ | CH₃ | p-Cl—Ph | 89 |
| PhOCH₂ | CH₃ | Ph | 90 |
| PhOCH₂ | p-CH₃O—PhCH₂ | Ph | 95 |

EXAMPLE 7

A 1.0 g quantity of benzyl 2-(3-phenoxyacetamido-4-benzenesulfonylthio-2-azetidinone-1-yl)-3-methyl-3-butenate was dissolved in 10 ml of dioxane. To the solution was added 3 g of NaHCO₃ and the mixture was stirred at room temperature. Into the reaction mixture was forced 1.5 equivalents of chlorine gas and the mixture was stirred for 2 hours. The same subsequent procedure as in Example 4 was conducted, giving 1.0 g of benzyl 2-(3-phenoxyacetamido-4-benzenesulfonylthio-2-azetidinone-1-yl)-3-chloromethyl-3-butenate in 95% yield.

EXAMPLE 8

A 200 mg quantity of benzyl 2-(3-phenoxyacetamido-4-benzenesulfonylthio-2-azetidinone-1-yl)-3-methyl-3-butenate was dissolved in 5 ml of ethoxyethyl acetate. The solution was cooled in an ice bath with stirring. Thereto was added dropwise over 10 minutes 1.21 ml of a 0.285M solution of Cl₂O in carbon tetrachloride. Water was added to the reaction mixture and the resulting mixture was extracted with ethyl acetate and dried over anhydrous magnesium sulfate. The solvent was distilled off at reduced pressure. The resulting residue was separated and purified by silica gel column chromatography, giving 202 mg of benzyl 2-(3-phenoxyacetamido-4-benzenesulfonylthio-2-azetidinone-1-yl)-3-chloromethyl-3-butenate in 95% yield.

EXAMPLE 9

A 2 g quantity of benzyl 2-(3-phenoxyacetamido-4-benzenesulfonylthio-2-azetidinone-1-yl)-3-methyl-3-butenate was dissolved in 12 ml of ethoxyethyl acetate. To the solution was added 6 g of NaHCO₃ and the mixture was stirred at room temperature. Thereto was added dropwise over 1 hour 12.1 ml of a 0.285M solution of Cl₂O in carbon tetrachloride. Water was added to the reaction mixture and the mixture was extracted with ethyl acetate and dried over anhydrous magnesium sulfate. The solvent was distilled off at reduced pressure. The resulting residue was separated and purified by silica gel column chromatography, giving 2.0 g of benzyl 2-(3-phenoxyacetamido-4-benzenesulfonylthio-2-azetidinone-1-yl)-3-chloromethyl-3-butenate in 94% yield.

EXAMPLE 10

The procedure of Example 9 was repeated using the solvents as shown below in Table 5, producing benzyl 2-(3-phenoxyacetamido-4-benzenesulfonylthio-2-azetidinone-1-yl)-3-chloromethyl-3-butenate in the yields as indicated below in Table 5.

TABLE 5

| Solvent | Yield (%) |
| --- | --- |
| Diethyl ether | 85 |
| Tetrahydrofuran | 90 |
| Dioxane | 92 |
| Dibutyl ether | 88 |
| Ethyl acetate | 90 |
| 1,2-Diacetoxyethane | 83 |
| 1,2-Dibenzyloxyethane | 89 |
| 1,2-Dibutoxyethane | 88 |
| 1,2-Diethoxyethane | 90 |
| 1,2-Dimethoxyethane | 92 |

EXAMPLE 11

The compounds as shown below in Table 6 were prepared in the same manner as Example 9 in the yields as indicated therein.

TABLE 6

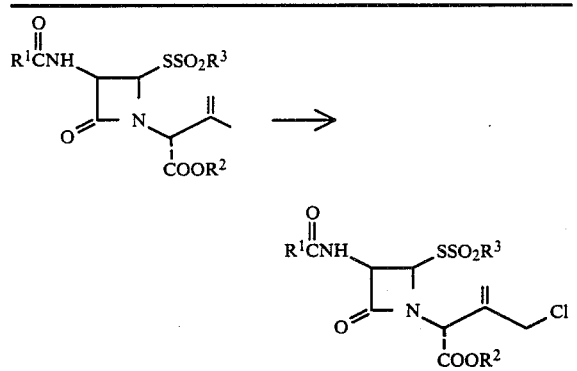

| R¹ | R² | R³ | Yield (%) |
|---|---|---|---|
| PhOCH$_2$ | PhCH$_2$ | p-CH$_3$—Ph | 90 |
| PhOCH$_2$ | PhCH$_2$ | p-NO$_2$—Ph | 93 |
| PhCH$_2$ | CH$_3$ | p-Cl—Ph | 89 |
| PhCH$_2$ | p-NO$_2$—PhCH$_2$ | p-NO$_2$—Ph | 95 |
| PhCH$_2$ | p-CH$_3$O—PhCH$_2$ | Ph | 92 |
| PhCH$_2$ | PhCH$_2$ | Ph | 88 |
| PhCH$_2$ | CCl$_3$CH$_2$ | p-NO$_2$—Ph | 85 |

EXAMPLE 12

A 200 mg quantity of benzyl 2-(3-phenoxyacetamido-4-benzenesulfonylthio-2-azetidinone-1-yl)-3-methyl-3-butenate was dissolved in 4.3 ml of diethoxyethane. The solution was cooled in an ice bath with stirring. Thereto was added dropwise over 3 minutes 1.73 ml of a 0.3M solution of HOCl in diethyl ether. Water was added to the reaction mixture and the resulting mixture was extracted with ethyl acetate and dried over anhydrous magnesium sulfate. The solvent was distilled off at reduced pressure. The resulting residue was separated and purified by silica gel column chromatography, giving 191 mg of benzyl 2-(3-phenoxyacetamido-4-benzenesulfonylthio-2-azetidinone-1-yl)-3-chloromethyl-3-butenate in 90% yield.

EXAMPLE 13

The procedure of Example 12 was repeated using the solvents as shown below in Table 7, giving benzyl 2-(3-phenoxyacetamido-4-benzenesulfonylthio-2-azetidinone-1-yl)-3-chloromethyl-3-butenate in the yields as indicated in the table.

TABLE 7

| Solvent | Yield (%) |
|---|---|
| Ethyl acetate | 90 |
| Dioxane | 91 |
| Diethyl ether | 89 |
| 1,2-Dibenzyloxyethane | 83 |
| 1,2-Diacetoxyethane | 85 |

EXAMPLE 14

A 200 mg quantity of benzyl 2-(3-phenoxyacetamido-4-benzenesulfonylthio-2-azetidinone-1-yl)-3-methyl-3-butenate was dissolved in 6 ml of benzene. To the solution was added with stirring 51 μl of t-BuOCl at room temperature and the mixture was further agitated for 1 hour. Water was added to the reaction mixture and the resulting mixture was subjected to the same subsequent procedure as in Example 12, giving 19.2 mg of benzyl 2-(3-phenoxyacetamido-4-benzenesulfonylthio-2-azetidinone-1-yl)-3-chloromethyl-3-butenate in 90% yield.

EXAMPLE 15

The procedure of Example 14 was repeated using the solvents as shown below in Table 8, producing benzyl 2-(3-phenoxyacetamido-4-benzenesulfonylthio-2-azetidinone-1-yl)-3-chloromethyl-3-butenate in the yields as indicated in the table. Table 8 also shows the reaction time.

TABLE 8

| Solvent | Reaction time (hr) | Yield (%) |
|---|---|---|
| Chlorobenzene | 12 | 90 |
| Ethyl acetate | 4 | 90 |
| Dioxane | 4 | 94 |
| 1,2-Dibutoxyethane | 1 | 88 |
| 1,2-Diethoxyethane | 0.5 | 92 |
| 1,2-Diacetoxyethane | 1 | 85 |
| 1,2-Dibenzyloxyethane | 1 | 87 |
| Ethoxyethyl acetate | 2.5 | 89 |

EXAMPLE 16

A 1.0 g quantity of p-nitrobenzyl 2-(3-phenylacetamido-4-benzenesulfonylthio-2-azetidinone-1-yl)-3-methyl-3-butenate was dissolved in 25 ml of ethoxyethyl acetate. The solution was cooled in an ice bath with stirring. To the mixture was added dropwise over 20 minutes 6.1 ml of a 0.285M solution of Cl$_2$O in carbon tetrachloride. Water was added to the reaction mixture and the mixture was extracted with ethyl acetate and dried over anhydrous magnesium sulfate. The solvent was distilled off at reduced pressure. The resulting residue was separated and purified by silica gel column chromatography, giving 955 mg of p-nitrobenzyl 2-(3-phenylacetamido-4-benzenesulfonylthio-2-azetidinone-1-yl)-3-chloromethyl-3-butenate in 90% yield.

EXAMPLE 17

The compounds as shown below in Table 9 were prepared in the same manner as Example 16 in the yields as indicated therein.

TABLE 9

$R^1CONH$, $SSO_2R^3$ azetidinone with N-CH(COOR²)-C(=CH₂)CH₃ → $R^1CONH$, $SSO_2R^3$ azetidinone with N-CH(COOR²)-C(=CHCl derivative)

| R¹ | R² | R³ | Yield (%) |
|---|---|---|---|
| PhCH₂— | 9-fluorenyl-CH | Ph | 89 |
| PhCH₂— | —CH₂-(2-NO₂-C₆H₄) | Ph | 91 |
| PhOCH₂— | 9-fluorenyl-CH | Ph | 90 |
| PhOCH₂— | —CH₂OCH₂CH₂OCH₃ | Ph | 90 |
| PhOCH₂— | —CH₂OCH₂OCH₃ | Ph | 89 |
| PhOCH₂ | —CH₂-(2,5-Cl₂-3,4,6-(OCH₃)₃-C₆) | Ph | 90 |

TABLE 9-continued

| R¹ | R² | R³ | Yield (%) |
|---|---|---|---|
| PhOCH₂ | —CH₂C(=O)-C₆H₄-Br | Ph | 85 |
| PhOCH₂ | —CH(COCH₃)(CO₂CH₃) | Ph | 88 |

EXAMPLE 18

Dissolved in 10 ml of benzene-dioxane (1:2) mixture was 1.0 g of methyl 2-(3-phenylacetamido-4-methylsulfonylthio-2-acetidinone-1-yl)-3-methyl-3-butenate. A 3 g quantity of NaHCO₃ was added to the solution. The mixture was stirred at room temperature. Thereto was added dropwise over 3 minutes a 1.5 ml of a 2.1 mmol solution of chlorine in carbon tetrachloride and the mixture was stirred for 2 hours. The reaction mixture was extracted with ethyl acetate and the extract was treated in the same manner as in Example 1, giving 0.96 g of methyl 2-(3-phenylacetamido-4-methylsulfonylthio-2-azetidinone-1-yl)-3-chloromethyl-3-butenate in 89% yield.

EXAMPLE 19

The procedure of Example 18 was repeated by using methyl 2-(benzoylamino-4-tert-butylbenzenesulfonylthio-2-azetidinone-1-yl)-3-methyl-3-butenate, producing methyl 2-(3-benzoylamino-4-tert-butylbenzenesulfonylthio-2-azetidinone-1-yl)-3-chloromethyl-3-butenate in 88% yield.

Table 10 below shows the properties of the compounds obtained in the foregoing examples.

TABLE 10

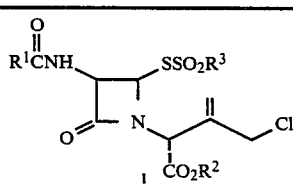

| R¹ | R² | R³ | IR (cm⁻¹) | NMR (δ, ppm) |
|---|---|---|---|---|
| PhOCH₂ | PhCH₂ | Ph | 3400, 1783, 1742, 1679, 1144, 1078, 755 | 4.09 and 4.15 (2H, ABq, J=13.3Hz), 4.45 (2H, bs), 4.78 (1H, bs) 5.20 (5H, bs), 5.95 (1H, d, J=5.3Hz), 6.60–7.80 (16H, m) |

TABLE 10-continued

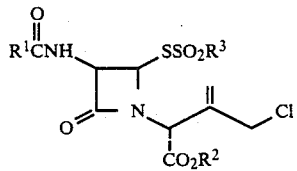

| R[1] | R[2] | R[3] | IR (cm$^{-1}$) | NMR (δ, ppm) |
|---|---|---|---|---|
| PhOCH$_2$ | PhCH$_2$ | p-NO$_2$—Ph | 3400, 1782, 1742, 1691, 1602, 1535, 1500, 1352, 1240, 1150, 1080, 860 | 4.12 (2H, bs), 4.41 (2H, bs), 4.70 (1H, s), 5.15 (5H, bs), 6.05 (1H, d, J=5Hz), 6.6–7.4 (10H, m), 7.61 (1H, d, J=7.6Hz), 7.90 (2H, d, J=9Hz), 8.15 (2H, d, J=9Hz) |
| PhOCH$_2$ | PhCH$_2$ | p-CH$_3$—Ph | 3380, 1780, 1740, 1678, 1331, 1140, 1076, 752 | 2.36 (3H, s), 4.09 and 4.14 (2H, ABq, J=13.3Hz), 4.41 (2H, bs), 4.85 (1H, bs), 5.18 (5H, m), 5.91 (1H, d, J=5.3Hz), 6.60–7.70 (15H, m) |
| PhOCH$_2$ | CH$_3$ | Ph | 3360, 1780, 1740, 1655, 1600, 1520, 1490, 1440, 1322, 1235, 1135, 1070, 900 | 3.72 (3H, s), 4.10 (2H, bs), 4.40 (2H, s), 4.82 (1H, s), 5.10–5.35 (3H, m), 5.94 (1H, d, J=6.6Hz), 6.70–8.00 (11H, m) |
| PhOCH$_2$ | p-CH$_3$O—PhCH$_2$ | Ph | 3400, 1780, 1740, 1675, 1613, 1600 | 3.77 (3H, s), 4.00 and 4.15 (2H, ABq, J=13Hz), 4.41 (2H, bs), 4.75 (1H, bs), 5.15 (5H, m), 5.90 (1H, d, J=5Hz), 6.70–7.90 (15H, m) |
| PhCH$_2$ | CH$_3$ | Ph | 3400, 1790, 1750, 1680, 1510, 1335, 1150, 1080 | 3.52 (2H, s), 3.70 (s, 3H), 4.10 (2H, bs), 4.80 (1H, s), 5.01 (1H, dd, J=4.4Hz and 7.8Hz), 5.10 (1H, s), 5.23 (1H, s), 5.87 (1H, d, J=4.4Hz), 6.71 (1H, d, J=7.8Hz), 7.22 (5H, s), 7.30–7.90 (m, 5H) |
| PhCH$_2$ | CH$_3$ | p-CH$_3$Ph | 3380, 1790, 1750, 1675, 1330 | 2.45 (3H, s), 3.55 (2H, s), 3.75 (3H, s), 4.13 (2H, bs), 4.92 (1H, s), 5.10 (1H, dd, J=4.4Hz and 7.8Hz), 5.10 (1H, s), 5.32 (1H, s), 5.80 (1H, d, J=4.4Hz), 6.45 (1H, d, J=7.8Hz), 7.25 (5H, s), 7.27 (2H, d, J=8Hz), 7.70 (2H, d, J=8Hz) |
| PhCH$_2$ | CH$_3$ | p-Cl—Ph | 3400, 1790, 1750, 1675, 1600 | 3.53 (2H, s), 3.73 (3H, s), 4.15 (2H, bs), 4.89 (1H, s), 5.03 (1H, dd, J=5Hz and 7.2Hz) 5.13 (1H, s), 5.32 (1H, s), 5.85 (1H, d, J=5Hz), 6.63 (1H, d, J=7.2Hz), 7.17 (5H, s), 7.48 (2H, d, J=10Hz), 7.75 (2H, d, J=10Hz) |
| PhCH$_2$ | CH$_3$ | p-NO$_2$—Ph | 3400, 1780, 1745, 1673, 1603, 1350, 1146, 1075, 850 | 3.57 (2H, s), 3.76 (3H, s), 4.17 (2H, bs), 4.90 (1H, s), 5.05 (1H, dd, J=4.4Hz and 7Hz), 5.18 (1H, s), 5.35 (1H, s), 5.94 (1H, d, J=4.4Hz), 6.50 (1H, d, J=7Hz), 7.28 (5H, s), 7.98 (2H, d, J=8Hz), 8.37 (2H, d, J=8Hz) |
| PhCH$_2$ | CH$_3$ | o-NO$_2$—Ph | 3400, 1780, 1747, 1680, 1603, 1350, 1150, 1025, 855 | 3.58 (2H, s), 3.80 (3H, s), 4.22 (2H, bs), 5.00 (1H, s), 5.10 (1H, dd, J=4.4Hz and 7.8Hz), 5.25 (1H, s), 5.35 (1H, s), 6.15 (1H, d, J=4.4Hz), 6.40 (1H, d, J=7.8Hz), 7.00–8.30 (9H, m) |
| PhCH$_2$ | PhCH$_2$ | Ph | 3400, 1780, 1745, 1680, 1500, 1450, 1150, 1080, 908, 850 | 3.54 (2H, s), 4.06 and 4.18 (2H, ABq, J=13Hz), 4.74 (1H, s), 5.05 (1H, dd, J=5Hz and 7.6Hz), 5.18 (4H, s), 5.90 (1H, d, J=5Hz), 6.64 (1H, d, J=7.6Hz), 7.20–8.00 (15H, m) |

TABLE 10-continued

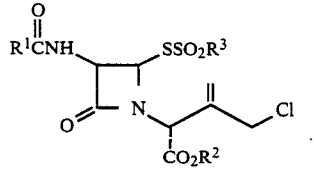

| R¹ | R² | R³ | IR (cm$^{-1}$) | NMR (δ, ppm) |
|---|---|---|---|---|
| PhCH$_2$ | PhCH$_2$ | p-CH$_3$O—Ph | 3395, 1780, 1740, 1675, 1500, 1333, 1260, 1140, 1080, 1025, 838 | 3.55 (2H, s), 3.75 (3H, s), 4.12 (2H, bs), 4.96 (1H, s), 5.10 (1H, dd, J=4.6Hz and 8Hz), 5.21 (3H, s), 5.31 (1H, s), 5.75 (1H, d, J=4.6Hz), 6.55 (1H, d, J=8Hz), 6.96 (2H, d, J=9Hz), 7.26 (5H, s), 7.40 (5H, s), 7.75 (2H, d, J=9Hz) |
| PhCH$_2$ | PhCH$_2$ | p-NO$_2$—Ph | 3400, 1790, 1744, 1680, 1603, 1355, 1150, 1080, 876 | 3.55 (2H, s), 4.15 (2H, bs), 4.97 (1H, s), 5.03 (1H, dd, J=5Hz and 8Hz), 5.20 (4H, bs), 5.95 (1H, d, J=5Hz), 6.80 (1H, d, J=8Hz), 7.28 (5H, s), 7.40 (5H, s), 7.95 (2H, d, J=9Hz), 8.26 (2H, d, J=9Hz) |
| PhCH$_2$ | CCl$_3$CH$_2$ | p-NO$_2$—Ph | 3410, 1792, 1680, 1358, 1150, 1080, 860 | 3.55 (2H, s), 4.23 (2H, s), 4.79 and 4.91 (2H, ABq, J=12Hz), 5.14 (1H, dd, J=5Hz and 8Hz), 5.24 (1H, s), 5.35 (1H, s), 5.50 (1H, s), 5.94 (1H, d, J=5Hz), 6.75 (1H, d, J=8Hz), 7.32 (5H, s), 8.01 (2H, d, J=9Hz), 8.38 (2H, d, J=9Hz) |
| PhCH$_2$ | p-NO$_2$—PhCH$_2$ | p-NO$_2$—Ph | 3400, 1790, 1745, 1680 | 3.48 (2H, s), 4.10 (2H, bs), 4.80–5.30 (6H, m), 5.82 (1H, d, J=5Hz), 6.70 (1H, d, J=7Hz), 7.13 (5H, s), 7.38 (2H, d, J=9Hz), 7.85 (2H, d, J=8.5Hz), 8.02 (2H, d, J=9Hz), 8.14 (2H, d, J=8.5Hz) |
| PhCH$_2$ | p-CH$_3$O—PhCH$_2$ | Ph | 3398, 1782, 1741, 1678, 1613, 1513, 1448, 1330, 1242, 1144, 1078 | 3.53 (s, 2H), 3.78 (s, 3H), 4.00 and 4.13 (ABq, 2H, J=12Hz), 4.19 (s, 1H), 5.00 (dd, 1H, J=4.8Hz and 8Hz), 5.07 (bs, 4H), 5.80 (d, 1H, J=4.8Hz), 6.32 (d, 1H, J=8Hz), 6.82 (d, 2H, J=9Hz), 7.00–7.90 (m, 12H) |
| PhCH$_2$— | 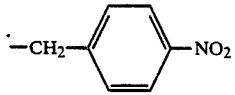 | Ph | | 3.55 (s, 2H), 4.08 and 4.15 (ABq, 2H, J=10Hz), 4.86 (s, 1H), 5.01 (dd, 1H, J=4.5 and 6.5Hz), 5.11 (s, 1H), 5.25 (s, 2H), 5.28 (s, 1H), 5.75 (d, 1H, J=4.5Hz), 6.08 (d, 1H, J=6.5Hz), 7.10–7.90 (m, 12H), 8.16 (d, 2H, J=7Hz) |
| PhCH$_2$— | 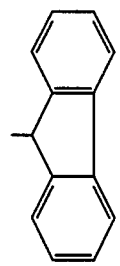 | Ph | | 3.58 (s, 2H). 4.05 and 4.13 (ABq, 2H, J=10Hz), 5.01 (s, 1H), 5.08 (dd, 1H, J=5 and 8Hz), 5.17 (s, 1H), 5.27 (s, 1H), 5.81 (d, 1H, J=5Hz), 5.96 (d, 1H, J=8Hz), 6.76 (s, 1H), 7.10–7.90 (m, 18H) |
| PhCH$_2$— | 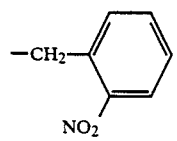 | Ph | | 3.58 (s, 2H), 4.09 and 4.14 (Abq, 2H, J=10Hz), 4.88 (s, 1H), 5.05 (dd, 1H, J=4.5 and 7Hz), 5.14 (s, 1H), 5.27 (s, 1H), 5.55 (s, 2H), 5.73 (d, 1H, J=4.5Hz), 6.10 (d, 1H, J=7Hz), 7.10–8.15 (m, 14H) |

TABLE 10-continued $$\underset{O}{\overset{R^1CNH}{\underset{\|}{\bigg|}}}\overset{SSO_2R^3}{\underset{N}{\bigcap}}\overset{}{\underset{CO_2R^2}{\bigg|}}\overset{}{\underset{}{\bigg\|}}Cl$$

| R¹ | R² | R³ | IR (cm⁻¹) | NMR (δ, ppm) |
|---|---|---|---|---|
| PhOCH₂— | (9-fluorenyl) | Ph | | 4.10 and 4.16 (ABq, 2H, J=10Hz),<br>4.43 and 4.47 (ABq, 2H, J=12Hz), 5.08 (s, 1H),<br>5.20 (s, 1H), 5.28 (dd, 1H, J=5 and 8Hz),<br>5.32 (s, 1H), 5.94 (d, 1H, J=5Hz), 6.65–7.85 (m, 20H) |
| PhOCH₂— | —CH₂OCH₂CH₂<br>\|<br>OCH₃ | Ph | | 3.37 (s, 3H), 3.40–3.65 (m, 2H), 3.65–3.85 (m, 2H),<br>4.09 and 4.14 (ABq, 2H, J=10Hz), 4.42 (s, 2H),<br>4.92 (s, 1H), 5.12 (s, 1H), 5.15–5.50 (m, 4H),<br>5.88 (d, 1H, J=5Hz), 6.75–7.90 (m, 11H) |
| PhOCH₂— | —CH₂OCH₃ | Ph | | 3.45 (s, 3H), 4.13 and 4.19 (ABq, 2H, J=11Hz),<br>4.44 (s, 2H), 4.93 (s, 1H), 5.15–5.45 (m, 5H),<br>5.98 (d, 1H, J=5Hz), 6.80–7.95 (m, 11H) |
| PhOCH₂— | —CH₂—(2,5-Cl₂-3,4,6-(OCH₃)₃-phenyl) | Ph | | 3.90 (s, 6H), 3.95 (s, 3H),<br>4.04 and 4.14 (ABq, 2H, J=9.5Hz), 4.44 (s, 2H),<br>4.85 (s, 1H), 5.05–5.30 (m, 3H), 5.44 (s, 2H),<br>5.95 (d, 1H, J=5Hz), 6.80–7.90 (m, 11H) |
| PhOCH₂— | —CH₂C(O)—C₆H₄—Br | Ph | | 4.10 and 4.16 (Abq, 2H, J=10Hz), 4.40 (s, 2H),<br>5.10–5.40 (m, 6H), 5.92 (d, 1H, J=5Hz),<br>6.75–7.90 (m, 15H) |
| PhOCH₂— | —CH(COCH₃)(CO₂CH₃) | Ph | | 2.90 (s, 3H), 3.72 (s, 2H), 3.89 (s, 3H),<br>4.17 (s, 2H), 4.47 (s, 2H), 5.20–5.70 (m, 5H),<br>5.88 (d, 1H, J=5Hz), 6.80–7.95 (m, 11H) |

We claim:

1. A process for preparing an azetidinone derivative represented by the formula (I)

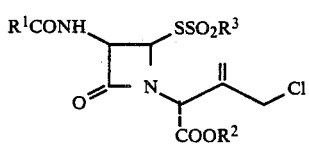

wherein R¹ represents an aryl group, arylmethyl group or aryloxymethyl group, R² represents hydrogen atom or a carboxyl-protecting group and R³ represents an alkyl group or aryl group, the process comprising reacting an azetidinone derivative represented by the formula (II)

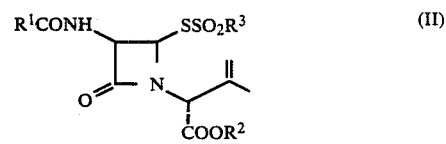

Wherein R¹, R² and R³ are as defined above with a chlorinating agent selected from the group Cl₂, R⁴OCl wherein R⁴ represents an alkyl group, HOCl and Cl₂O.

2. A process as defined in claim 1 wherein the chlorinating agent is Cl₂O.

3. A process as defined in claim 1 in which the chlorinating agent is dissolved in an inert organic solvent.

4. A process as defined in any claim 1 in which the chlorinating agent is used in an amount of about 1 to about 7 equivalents relative to the compound (II).

5. A process as defined in claim 1 in which the reaction is conducted in a solvent.

6. A process as defined in claim 5 in which the solvent is one species or a mixture of two or more species selected from the group consisting of halogenated lower hydrocarbon, aromatic hydrocarbon, di-lower alkyl-ether, cyclic ether, di-lower alkoxy-ethane and ester of lower carboxylic acid.

7. A process as defined in claim 5 in which the solvent is one species or a mixture of two or more species selected from the group consisting of chloroform, dichloromethane, dichloroethane, carbon tetrachloride, benzene, chlorobenzene, dimethyl ether, diethyl ether, tetrahydrofuran, dioxane, 1,2-dimethoxyethane, 1,2-diethoxyethane, 1,2-dibutoxyethane, 1,2-dibenzyloxyethane, 1,2-diacetoxyethane, ethyl formate, ethyl acetate and 1,2-diacetoxyethane, ethyl formate, ethyl acetate and ethoxyethyl acetate.

8. A process as defined in claim 5 in which the solvent contains at least a hydrophobic organic solvent and water.

9. A process as defined in claim 8 in which the hydrophobic organic solvent is at least one of the species selected from the group consisting of chloroform, dichloromethane, dichloroethane, carbon tetrachloride, benzene, chlorobenzene, and ethyl acetate.

10. A process as defined in any claim 1 in which the reaction is carried out in the presence of a compound capable of trapping hydrogen chloride.

11. A process as defined in any claim 1 in which the reaction is carried out at a temperature of about $-70°$ and about 70° C.

12. A process as defined in claim 1 wherein the chlorinating agent is $Cl_2$.

* * * * *